United States Patent
Nash

(10) Patent No.: US 10,568,352 B1
(45) Date of Patent: Feb. 25, 2020

(54) NUTRITIONAL COMPOSITIONS AND METHODS OF TREATMENT THEREWITH

(71) Applicant: Wiser Concepts, LLC, Versailles, KY (US)

(72) Inventor: Delia Nash, Versailles, KY (US)

(73) Assignee: Wiser Concepts, LLC, Versailles, KY (US)

(*) Notice: Subject to any disclaimer, the term of this patent is extended or adjusted under 35 U.S.C. 154(b) by 0 days.

(21) Appl. No.: 16/170,492

(22) Filed: Oct. 25, 2018

(51) Int. Cl.
| | |
|---|---|
| *A23L 33/175* | (2016.01) |
| *A23L 33/105* | (2016.01) |
| *A61K 31/198* | (2006.01) |
| *A61K 31/05* | (2006.01) |
| *A61K 9/00* | (2006.01) |
| *A61P 3/04* | (2006.01) |

(52) U.S. Cl.
CPC .......... *A23L 33/175* (2016.08); *A23L 33/105* (2016.08); *A61K 9/0053* (2013.01); *A61K 31/05* (2013.01); *A61K 31/198* (2013.01); *A61P 3/04* (2018.01); *A23V 2002/00* (2013.01); *A23V 2200/332* (2013.01); *A23V 2250/063* (2013.01); *A23V 2250/0628* (2013.01); *A23V 2250/2132* (2013.01); *A23V 2250/21168* (2013.01)

(58) Field of Classification Search
CPC .................................................. A61K 31/198
See application file for complete search history.

(56) References Cited

U.S. PATENT DOCUMENTS

| | | | |
|---|---|---|---|
| 8,617,886 B2 | 12/2013 | Zemel et al. | |
| 9,072,692 B2 | 7/2015 | Zemel et al. | |
| 9,198,454 B2 | 12/2015 | Zemel et al. | |
| 9,198,883 B1 | 12/2015 | Zemel et al. | |
| 9,351,967 B2 | 5/2016 | Zemel et al. | |
| 9,408,410 B2 | 8/2016 | Zemel et al. | |
| 9,408,834 B2 | 8/2016 | Zemel et al. | |
| 9,585,876 B2 | 3/2017 | Zemel et al. | |
| 9,682,053 B2 | 6/2017 | Zemel et al. | |
| 9,707,213 B2 | 7/2017 | Zemel et al. | |
| 9,713,609 B2 | 7/2017 | Zemel et al. | |
| 9,724,319 B2 | 8/2017 | Zemel et al. | |
| 9,737,501 B2 | 8/2017 | Zemel et al. | |
| 9,855,235 B2 | 1/2018 | Zemel et al. | |
| 9,872,844 B2 | 1/2018 | Zemel et al. | |
| 9,895,357 B2 | 2/2018 | Zemel et al. | |
| 9,901,573 B2 | 2/2018 | Zemel et al. | |
| 9,943,517 B2 | 4/2018 | Zemel et al. | |
| 10,039,733 B2 | 8/2018 | Zemel et al. | |
| 10,076,507 B1 | 9/2018 | Zemel et al. | |
| 2005/0171027 A1* | 8/2005 | Sinclair ................. | A61K 31/00 514/25 |

(Continued)

OTHER PUBLICATIONS

Bruckbauer et al., Nutrition & Metabolism, 2012,9:77 (Year: 2012).*

(Continued)

*Primary Examiner* — San Ming R Hui
(74) *Attorney, Agent, or Firm* — Bradley Arant Boult Cummings; Timothy L. Capria

(57) ABSTRACT

The disclosure provides nutritional compositions including a blend of amino acids and polyphenols. These nutritional compositions find use, for example, in treating and preventing EMS and laminitis in equines, as well as generally promoting animal health.

20 Claims, 3 Drawing Sheets

(56) References Cited

U.S. PATENT DOCUMENTS

2011/0064720 A1 3/2011 Amato

OTHER PUBLICATIONS

Kalogeropoulou et al., Am J Clin Nutr, 2009;90:314-320 (Year: 2009).*

Gannon et al., Am J Clin Nutr, 2002;76:1302-1307 (Year: 2002).*

Ding et al., Amino Acis composition of lactating mothers' milk and confinement diet in rural North China, Asia Pacific Journal of Clinical Nutrition, 2010, 334-349,19-3, Hec Press, Australia.

Bruckbauer et al., Synergistic effects of leucine and resveratrol on insulin sensitivity and fat metabolism in adipocytes and mice, Nutrition & Metabolism, 2012, 9-77, BioMed Central Ltd., online.

Adams et al., Identifying the role of a "caloric restriction mimetic", in resveratrol, in Equine Metabolic Syndrome and its implications for targeted therapy, Journal of Equine Veterinary Science, 2013, 346-347, 33-5, Elsevier, online.

Frank et al., Equine Metabolic Syndrome, Journal of Veterinary Internal Medicine, 2010, 467-475, 24-3, John Wiley & Sons, online.

Frank et al., Insulin Dysregulation, Equine Veterinary Journal, 2014, 103-112, 46-1, John Wiley & Sons, online.

Bertin et al., The diagnosis of equine insulin dysregulation, Equine Veterinary Journal, 2017, 570-576, 49-5, John Wiley & Sons, online.

De Laat et al., Continuous intravenous infusion of glucose induces endogenous hyperinsulinaemia and lamellar histopathology in Standardbred horses, The Veterinary Journal, 2012, 317-322, 191-3, Elsevier, online.

De Laat et al. Equine hyperinsulinemia: investigation of the enteroinsular axis during insulin dysregulation, American Journal of Physiology Endocrinology and Metabolism, 2016, E61-E72, 310-1, American Physiological Society, online.

De Laat et al., Equine Laminitis: Comparative Histopathology 48 hours after Experimental Induction with Insulin or Alimentary Oligofructose in Standardbred Horses, Journal of Comparative Pathology, 2011, 399-409, 145-4, Elsevier, online.

Asplin et al., Induction of laminitis by prolonged hyperinsulinaemia in clinically normal ponies, The Veterinary Journal, 2007, 530-535, 174-3, Elsevier, online.

Geor et al., Dietary Management of Obesity and Insulin Resistance: Countering Risk for Laminitis, Veterinary Clinics of North America: Equine Practice, 2009, 51-65, 25-1, Elsevier, online.

Treiber et al., Glucose dynamics during exercise: dietary energy sources affect minimal model parameters in trained Arabian geldings during endurance exercise, Equine Veterinary Journal Supplemental Issue, 2006, 631-666, 36, John Wiley & Sons, online.

Morgan et al., Treatment of equine metabolic syndrome: A clinical case series, Equine Veterinary Journal, 2015, 422-426, 48-4, John Wiley & Sons, online.

Jacob et al., Effect of dietary carbohydrates and time of year on ACTH and cortisol concentrations in adult and aged horses, Domestic Animal Endocrinology, 2018, 15-22, 63, Elsevier, online.

Jacob et al., Effect of age and dietary carbohydrate profiles on glucose and insulin dynamics in horses, Equine Veterinary Journal, 2018, 249-254, 50-2, John Wiley & Sons, online.

Rapson et al., Effects of age and diet on glucose and insulin dynamics in the horse, Equine Veterinary Journal, 2018, 590-696, 50-5, John Wiley & Sons, online.

Rendle et al., Effects of metformin hydrochloride on blood glucose and insulin responses to oral dextrose in horses, Equine Veterinary Journal, 2013, 751-754, 45-6, John Wiley & Sons, online.

Durham, Therapeutics for Equine Endocrine Disorders, Veterinary Clinics of North America: Equine Practice, 2017, 127-139, 33-1, Elsevier, online.

Durham, Metformin in equine metabolic syndrome: An enigma or a dead duck?, The Veterinary Journal, 2012, 17-18, 191-1, Elsevier, online.

Tinworth et al., The effect of oral metformin on insulin sensitivity in insulin-resistant ponies, The Veterinary Journal, 2012, 79-84, 191-1, Elsevier, online.

McGowan et al., Dietary restriction in combination with a nutraceutical supplement for the management of equine metabolic syndrome in horses, The Veterinary Journal, 2013, 153-159, 196-2, Elsevier, online.

Hoffman et al., Obesity and diet affect glucose dynamics and insulin sensitivity in Thoroughbred geldings, Journal of Animal Science, 2003, 2333-2342, 81-9, Oxford Academic, online.

Tinworth et al., Pharmacokinetics of metformin after enteral administration in insulin-resistant ponies, American Journal of Veterinary Research, 2010, 1201-1206, 71-10, American Veterinary Medical Association, Chicago.

Hustace et al., Pharmacokinetics and bioavailability of metformin in horses, American Journal of Veterinary Research, 2009, 665-668, 70-5, American Veterinary Medical Association, Chicago.

Tome-Carneiro, et al., One-Year Consumption of a Grape Nutraceutical Containing Resveratrol Improves the Inflammatory and Fibrinolytic Status of Patients in Primary Prevention of Cardiovascular Disease, The American Journal of Cardiology, 2012, 356-363, 110-3, Elsevier, online.

Palsamy, et al., Resveratrol, a natural phytoalexin, normalizes hyperglycemia in streptozotocin-nicotinamide induced experimental diabetic rats, Biomedicine & Pharmacotherapy, 2008, 598-605, 62-9, Elsevier, online.

Schuver et al., Assessment of Insulin and Glucose Dynamics by Using an Oral Sugar Test in Horses, Journal of Equine Veterinary Science, 2014, 465-40, 34-4, Elsevier, online.

De Lucia Rolfe et al., Abdominal fat depots associated with insulin resistance and metabolic syndrome risk factors in black African young adults, BMC Public Health, 2015, 15-1, BioMed Central Ltd., online.

Jonas et al., Interleukins 6 and 15 Levels Are Higher in Subcutaneous Adipose Tissue, but Obesity Is Associated with Their Increased Content in Visceral Fat Depots, International Journal of Molecular Sciences, 2015, 25817-25830, 16-10, Molecular Diversity Preservation International and Multidisciplinary Digital Publishing Institute, Switzerland.

Smith, Abdominal obesity: a marker of ectopic fat accumulation, The Journal of Clinical Investigation, 2015, 1790-1792, 125-5, American Society for Clinical Investigation, online.

Selim et al., Relationships among Body Condition, Insulin Resistance and Subcutaneous Adipose Tissue Gene Expression during the Grazing Season in Mares, 2015, e0125968, 10-5, PLOS, online.

Bruynsteen et al., Expression of inflammation-related genes is associated with adipose tissue location in horses, BMC Veterinary Research, 2013, 240, 9-1, BioMed Central Ltd., online.

Frank et al., Repeatability of Oral Sugar Test Results, Glucagon-Like Peptide-1 Measurements, and Serum High-Molecular-Weight Adiponectin Concentrations in Horses, Journal of Veterinary Internal Medicine, 2017, 1178-1187, 31-4, John Wiley & Sons, online.

Romacho et al., Adipose tissue and its role in organ crosstalk, Acta Physiologica, 2014, 733-753, 210-4, Wiley-Blackwell, online.

Adams-Huet et al., Increased Adipose Tissue Insulin Resistance in Metabolic Syndrome: Relationship to Circulating Adipokines, Metabolic Syndrome and Related Disorders, 2014, Mary Ann Liebert, Inc., New York.

Yadav et al., Role of leptin and adiponectin in insulin resistance, Clinica Chimica Acta, 2013, 80-84, 417, Elsevier, online.

Wooldridge et al., Evaluation of high-molecular weight adiponectin in horses, American Journal of Veterinary Research, 2012, 1230-1240, 73-8, American Veterinary Medical Association, Chicago.

Bamford et al., Effect of increased adiposity on insulin sensitivity and adipokine concentrations in different equine breeds adapted to cereal-rich or fat-rich meals, The Veterinary Journal, 2016, 14-20, 214, Elsevier, online.

Carter et al., Prediction of incipient pasture-associated laminitis from hyperinsulinaemia, hyperleptinaemia and generalised and localised obesity in a cohort of ponies, Equine Veterinary Journal, 2009, 171-178, 41-2, John Wiley & Sons, online.

(56) References Cited

OTHER PUBLICATIONS

De Laat, Equine laminitis: Induced by 48 h hyperinsulinaemia in Standardbred horses, Equine Veterinary Journal, 2010, 129-135, 42-2, John Wiley & Sons, online.

Karikoski et al., Pathology of Natural Cases of Equine Endocrinopathic Laminitis Associated With Hyperinsulinemia, Veterinary Pathology, 2015, 945-956, 52-5, SAGE Publications, online.

* cited by examiner

NUTRITIONAL COMPOSITIONS AND METHODS OF TREATMENT THEREWITH

This is a Non-Provisional Patent Application for the invention by Delia Nash, a citizen of the United States, residing in Versailles, Ky., for "NUTRITIONAL COMPOSITIONS AND METHODS OF TREATMENT THEREWITH."

BACKGROUND

A. Field of the Disclosure

The present disclosure relates generally to nutritional compositions and methods of treatment and/or prevention of diseases and medical conditions, particularly to those diseases and medical conditions that afflict animals such as equines.

B. Background

Many horses are affected by equine metabolic syndrome (EMS) and similar pathologies, which are often characterized by the equine's inability to normally regulate insulin. As a result, equines having EMS often develop obesity, as they store excess fat in the crest, neck, and shoulder areas. It is also thought that obesity may increase the risk of the onset of EMS. Other symptoms associated with EMS include hypertension and elevated blood triglyceride levels. EMS can lead to the development of laminitis, a foot disease in ungulates (e.g., equines and bovines). If the laminitis progresses, the animal may be unable to stand and require euthanasia. However, EMS and laminitis are difficult to treat, often requiring complicated treatments such as the administration of pharmaceuticals. Thus, a need exists for better ways to prevent and treat EMS and laminitis, as well as generally promote animal health.

BRIEF SUMMARY

The disclosure provides nutritional supplements and compositions for administration to a subject, such as a horse. These compositions and supplements find use, for example, in treating or preventing equine metabolic syndrome or equine insulin dysregulation.

In a first aspect, a nutritional supplement is disclosed. The nutritional supplement comprises leucine in an amount of 0.5% to 25% of the nutritional composition by weight, resveratrol in an amount of 0.2% to 20% of the nutritional supplement by weight, and one or more amino acids including alanine, glutamic acid, glycine, proline, or a combination thereof. The resveratrol may be in amount of from 0.5% to 10%, from 1% to 3%, or about 2.5% of the nutritional supplement by weight. The leucine may be in amount of from 1% to 15%, from 2% to 10%, or about 7.5% of the nutritional supplement by weight.

The nutritional supplement may include lysine. The lysine may be present in the nutritional supplement in an amount of from 1% to 20%, from 3% to 10%, or about 6% of the nutritional supplement by weight.

The nutritional supplement may include quercetin. In some embodiments, the nutritional supplement includes dried yeast fermentation solubles. The nutritional supplement may be free, or substantially free of, leucine metabolites. The resveratrol may be provided in the nutritional supplement in an unencapsulated form or substantially free of a quercetin carrier.

The nutritional supplement may be an equine nutritional supplement. The nutritional supplement may enteral (e.g., for oral administration).

In a second aspect, a method of treating or preventing equine metabolic syndrome or equine insulin dysregulation in an equine in need thereof is provided. The method includes administering to the equine a nutritional composition including a therapeutically effect amount of leucine and resveratrol. The nutritional composition may be administered orally to the equine in an amount of from 2 g to 500 g per day, 5 g to 150 g per day, or from 15 g to 50 g per day.

In a third aspect, a method of treating or preventing an ailment in an equine is provided. The method includes administering a nutritional composition to the equine. The administered nutritional composition includes from 250 mg to 2,250 mg of resveratrol by weight of the nutritional composition, from 700 mg to 6,300 mg of leucine by weight of the nutritional composition, and from 580 mg to 5,220 mg of lysine by weight of the nutritional composition. The nutritional composition may be administered to the equine orally on a daily dosage regimen. The nutritional composition may be mixed with equine feed prior to the administration to the equine.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

DETAILED DESCRIPTION

Figure 1:
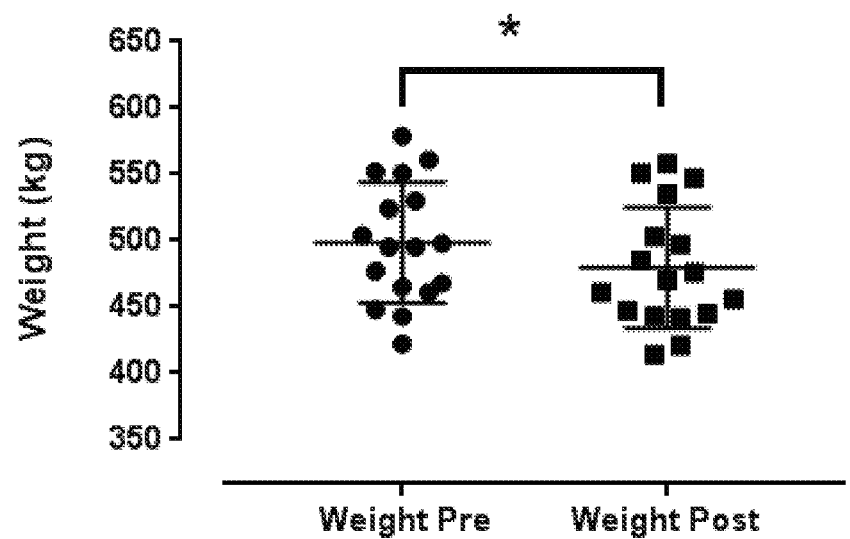
FIG. 1. Weight (kg) both pre- and post-SPAAB+L supplementation. * indicates significant at $P<0.05$.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terminology used herein is for the purpose of describing particular embodiments only and is not intended to be limiting. As used herein, the singular forms "a", "an" and "the" are intended to include the plural forms as well, unless the context clearly indicates otherwise.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The term "consisting essentially of" means that, in addition to the recited elements, what is claimed may also contain other elements (steps, structures, ingredients, components, etc.) that do not adversely affect the operability of what is claimed for its intended purpose as stated in this disclosure. Importantly, this term excludes such other elements that adversely affect the operability of what is claimed for its intended purpose as stated in this disclosure, even if such other elements might enhance the operability of what is claimed for some other purpose.

The terms "about" and "approximately" shall generally mean an acceptable degree of error or variation for the quantity measured given the nature or precision of the measurements. Typical exemplary degrees of error or variation are within 20 percent (%), preferably within 10%, and more preferably within 5% of a given value or range of values. For biological systems, the term "about" refers to an acceptable standard deviation of error, preferably not more than 2-fold of a given value. Numerical quantities given herein are approximate unless stated otherwise, meaning that the term "about" or "approximately" can be inferred when not expressly stated.

The terms "prevention," "prevent," "preventing," "suppression," "suppress" and "suppressing" as used herein refer to a course of action (such as administering a pharmaceutical composition) initiated prior to the onset of a clinical manifestation of a disease state or condition so as to reduce the likelihood or severity. Such reduction in likelihood or severity need not be absolute to be useful.

The terms "treatment," "treat," and "treating" as used herein refers to a course of action (such as administering a pharmaceutical composition) initiated after the onset of a clinical manifestation of a disease state or condition so as to eliminate or reduce such clinical manifestation of the disease state or condition. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that include the knowledge that the patient is ill, or will be ill, as the result of a condition that is treatable by a method or device of the present disclosure.

The term "in need of prevention" as used herein refers to a judgment made by a caregiver that a patient requires or will benefit from prevention. This judgment is made based on a variety of factors that are in the realm of a caregiver's expertise, but that include the knowledge that the patient will be ill or may become ill, as the result of a condition that is preventable by a method or device of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "therapeutically effective amount" as used herein refers to an amount of a compound, either alone or as a part of a pharmaceutical composition, that is capable of having any detectable, positive effect on any symptom, aspect, or characteristics of a disease state or condition. Such effect need not be absolute to be beneficial.

The present disclosure provides a nutritional composition, such as a supplement, for administration to an animal. The nutritional composition may be formulated as a liquid, a gel, a pill form, a pellet, or in a dry granular form. Embodiments provided in a pellet form or a dry granular form may be particularly advantageous, as these embodiments may allow for the nutritional composition to be mixed with food from an animal's normal diet, such as commercially available horse feed, to enable convenient administration to the animal. Beneficially, mixing the nutritional composition with food from an animal's diet may improve digestion and bioabsorption of the nutritional composition in the animal. The nutritional composition may be provided as a concentrate.

The nutritional composition may be provided in scoopable form (e.g., granular) for periodic or single dose administration to the animal. In one embodiment, the nutritional composition is provided in a form for daily administration, such in an amount of from 2 g to 1,000 g, from 5 g to 500 g, from 10 g to 200 g, from 15 g to 50 g, about 28 g, or any subrange of subvalue thereof. In an embodiment, the nutritional composition is provided in a form for twice-daily administration, such in an amount of from 2 g to 500 g, from 2.5 g to 250 g, from 5 g to 100 g, from 7.5 g to 25 g, about 14 g, or any subrange of subvalue thereof.

An embodiment of the nutritional composition includes leucine. Leucine is a branched chain amino acid and is an essential amino acid in the diet of animals, as animals cannot synthesize it and must ingest it from other sources. Leucine may be present in the nutritional composition in an amount of from 0.5% to 25%, from 1% to 15%, from 2% to 10%, from 2% to 5% of the nutritional composition, about 7.5%, about 4%, or any subrange or subvalue thereof, of the nutritional composition by weight. In some embodiments of the nutritional composition, leucine is provided in an amount of from 200 mg to 21,000 mg, from 350 mg to 6,300 mg, from 500 mg to 4,200 mg, from 1,500 mg to 2,700 mg, about 2,100 mg, or any subrange or subvalue thereof, by weight of the nutritional composition. In an embodiment of the nutritional composition, leucine is provided in a free form—that is, not provided in proteins or as part of a polypeptide chain. Some embodiments of the nutritional composition include leucine provided as part of proteins and/or polypeptide chains.

One or more embodiments of the nutritional composition includes one or more polyphenols, such as flavonoids. The nutritional composition may include resveratrol, a naturally occurring polyphenol. Resveratrol may be present in the nutritional composition in an amount of from 0.2% to 20%, from 0.5% to 10%, from 1% to 3%, about 2.5%, or any subrange or subvalue thereof, of the nutritional composition by weight. In some embodiments of the nutritional composition, resveratrol is present in an amount of from 75 mg to 7,500 mg, from 250 mg to 2,250 mg, from 500 mg to 1,000 mg, about 750 mg, or any subrange or subvalue thereof, by weight of the nutritional composition.

Some embodiments of the nutritional composition include quercetin. Quercetin is a flavonoid and can be found in, for example, kale leaves and red onions. Quercetin may be present in the nutritional composition in an amount of from 0.1% to 15%, from 0.2% to 10%, from 0.5% to 5%, from 1% to 2.5%, from 1% to 2%, about 1.5%, or any subrange or subvalue thereof, of the nutritional composition by weight. In some embodiments of the nutritional composition, quercetin is present in an amount of from 50 mg to 5,000 mg, from 100 mg to 2,500 mg, from 250 mg to 1,000 mg, from 300 mg to 600 mg, about 500 mg, or any subrange or subvalue thereof, by weight of the nutritional composition.

The one or more polyphenols are provided in unencapsulated form or encapsulated form. Encapsulated resveratrol may be encapsulated in oil, such as grape seed oil, to improve its stability. However, it has been discovered that encapsulated resveratrol may have less bioavailability than unencapsulated resveratrol. Thus, in some embodiments, resveratrol is provided in the nutritional composition in unencapsulated form. The resveratrol may be free or substantially free of a resveratrol carrier (e.g., oil delivery systems).

An embodiment of the nutritional composition includes lysine. Lysine is a branched chain amino acid and is an essential amino acid in the diet of animals, as animals cannot synthesize it and must ingest it from other sources. Lysine may be present in the nutritional composition in an amount of from 0.2% to 20%, from 0.5% to 10%, from 4% to 6%, from 1% to 3%, about 6%, about 2.5%, or any subrange or subvalue thereof, of the nutritional composition by weight. In some embodiments of the nutritional composition, lysine is provided in an amount of from 175 mg to 17,500 mg, from 350 mg to 6,000 mg, from 500 mg to 4,000 mg, from 1,500 mg to 2,500 mg, about 1,740 mg, or any subrange or subvalue thereof, by weight of the nutritional composition. In an embodiment of the nutritional composition, lysine is provided in a free form—that is, not provided in proteins or as part of a polypeptide chain. Some embodiments of the nutritional composition include lysine provided as part of proteins and/or polypeptide chains.

Embodiments of the nutritional composition include additional amino acids, including one or more of alanine, arginine, asparagine, aspartic acid, cysteine, glutamine, glutamic acid, glycine, histidine, isoleucine, methionine, phenylalanine, proline, serine, threonine, tryptophan, tyrosine, or valine. In some embodiments, one or more of alanine, glutamic acid, glycine, or proline are included. Each of the additional amino acids may be present in the nutritional composition in an amount of 0.1% to 10%, from 0.25% to 7.5%, from 0.5% to 5%, from 0.75%-2.5%, about 2%, about 1%, or any subrange or subvalue thereof, by weight of the nutritional composition. In embodiments of the nutritional composition, the additional amino acids are present in an amount of from 25 mg to 5,000 mg, 50 mg to 3,000 mg, 75 mg to 2,000 mg, 100 mg to 1000 mg, 250 mg to 750 mg, about 250 mg, about 300 mg, about 400, about 500 mg, or any subrange or subvalue thereof, by weight of the nutritional composition. The additional amino acids may be provided in free form or as part of proteins and/or polypeptide chains.

Table 1 below shows amino acid content of an embodiment of the nutritional supplement.

TABLE 1

| Amino Acid | Amount Per 28 g of Nutritional Composition |
| --- | --- |
| Leucine | 2,100 mg |
| Lysine | 1,740 mg |

TABLE 1-continued

| Amino Acid | Amount Per 28 g of Nutritional Composition |
| --- | --- |
| Glutamic Acid | 1,010 mg |
| Proline | 470 mg |
| Alanine | 395 mg |
| Glycine | 250 mg |

The nutritional composition may further comprise vehicles, adjuvants, surfactants, suspending agents, emulsifying agents, inert fillers, diluents, excipients, wetting agents, binders, lubricants, buffering agents, disintegrating agents and carriers, as well as accessory agents, such as coloring agents and flavoring agents. Suitable flavoring agents may include one or more of apple, banana, cherry, carrot, cumin, fenugreek, rosemary, peppermint, or oregano.

The nutritional composition may further comprise one or more of: water; pH buffers; humectants (to prevent dry-out and increase pleasant mouth feel) such as, glycerin, sorbitol, polypropylene glycol, xylitol, and polyethylene glycol; thickeners such as silica thickeners, sodium aluminum silicates, and clays; gums such as sodium carboxymethyl cellulose, cellulose ethers, xantham gum, carrageenans, sodium alginate, and carbopols; antibacterial agents; flavoring agents such as, water-insoluble essential oils; sweetening agents such as, saccharin, dextrose, levulose, cyclamate, aspartate; coloring agents; and binders.

The nutritional composition may contain grain, molasses, vegetable oil, salt, and dried yeast fermentation solubles.

The nutritional composition may be free, or substantially free, of leucine metabolites (e.g., ketoisocaproic acid, β-Hydroxy β-methylbutyric acid, isovaleryl-coenzyme A, 3-methylcrotonyl-coenzyme A, acetoacetyl-coenzyme A, and acetyl-coenzyme A). As used herein, "substantially free of" means that only trace components of a particular component may be found in the composition. In an embodiment, "substantially free of" means less than 0.1% by weight of the nutritional composition. In some embodiments, substantially free of means less than 0.01% of the nutritional composition. In other embodiments, substantially free of means less than 0.001% of the nutritional composition.

The nutritional composition may be free of, or substantially free of, sirtuin pathway activators other than resveratrol and quercetin. The molar ratio of leucine and leucine metabolites to sirtuin pathway activators (e.g., resveratrol and quercetin) in the nutritional composition may be less than 10, less than 7.5, less than 5, less than 4, less than 3, less than 2, or less than 1.

A method for treating or preventing equine metabolic syndrome or equine insulin dysregulation in an equine in need thereof is provided. The method may include administering to the equine the nutritional composition described herein, the nutritional composition including a therapeutically effective amount of leucine and resveratrol. The therapeutically effective amount may vary according to a variety of factors such as the subject's condition, weight, sex, and age. For example, some embodiments of the composition comprise up to the median lethal dose (LD50) of the active compound. The LD50 can be ascertained using standard toxicological methods, or by reference to past studies. The method may include enteral (e.g., oral) administration to the equine. The nutritional composition may be orally administered to the equine in an amount of from 1 g to 1,000 g per day, 5 g to 150 g per day, from 15 g to 50 g per day, or about 28 g per day. The method may include contacting, or mixing, the nutritional composition with animal feed, such as equine feed, prior to administration. As used herein, the term "feed" refers to a composition for generally meeting the basic nutritional needs of an animal.

A method of treating or preventing an ailment in animals is provided. The animal, as used herein, may be, for example, a mammal, an ungulate, an equine, a pig, a camel, a deer, a mule, or a donkey. The method may include administering to the nutritional composition disclosed herein. The nutritional composition may include from 250 mg to 2,250 mg of resveratrol by weight of the nutritional composition, from 700 mg to 6,300 mg of leucine by weight of the nutritional composition, and from 580 mg to 5,220 mg of lysine by weight of the nutritional composition. The ailment may be selected from the group consisting of: equine metabolic syndrome, insulin dysregulation, obesity, high insulin levels, low high molecular weight adiponectin, pituitary pars intermedia dysfunction, altered insulin regulation, inflammation, joint disease, high blood pressure, allergies, a glycogen storage disease, and combinations thereof. The nutritional composition may be administered to the animal orally on a daily dose basis or a twice daily dose basis.

A method of improving the metabolism of an equine is provided, the method including administering to the equine the nutritional composition disclosed herein. Improving the metabolism may comprise improving performance or promoting the replenishment of energy (e.g., aiding in glycogen repletion and storage) after the equine has performed intensive exercise.

Working Example 1

Surprisingly, it has been discovered that polyphenol and the disclosed amino acid blend including leucine have an unexpected and synergistic effect. Indeed, when the diet of equines having insulin dysregulation (ID) or equine metabolic syndrome (EMS) was supplemented with the disclosed nutritional composition, the equines were found to have unexpectedly improved health parameters, such as lowering insulin and increasing high molecular weight (HMW) adiponectin. As high insulin and low molecular weight adiponectin are risk factors in the onset of laminitis, the nutritional composition and methods herein may be useful for preventing or reducing risk of laminitis.

Fifteen adult horses (6 Arabians, 9 Morgans, 10 geldings and 5 mares, average age 10±6 years, average weight 495±45 kg, average body condition score 7±0.8 out of 9) all previously tested to have insulin resistance (determined by an insulin modified frequently sampled intravenous glucose tolerance test) and/or insulin dysregulation (determined via an Oral Sugar Test (OST) were used. The horses were grouped into low (LOW) dose of once a day, in feed SPAAB+L supplement or high (HIGH) dose of once a day, in feed SPAAB+L supplement.

The LOW and HIGH horses had a baseline OST performed before starting either a low (LOW) or high (HIGH) dose of a once a day, in-feed SPAAB+L supplement. At the end of six weeks, both groups of horses repeated the OST. Body condition scores, presence of regional adiposity, history of laminitis, and weight were recorded pre- and post-supplement administration.

Horses were fasted from 10 pm the night before the tests were performed. The morning of the tests, IV catheters were placed in the jugular at least an hour before the test, and a baseline blood sample was drawn. Karo syrup light was administered as a bolus by mouth (0.25 mL/kg body weight (bwt)) and blood was drawn at 15, 30, 60, 75, 90, 120, 150, and 180 minutes post Karo syrup administration and placed in serum or lithium heparin tubes, centrifuged, and plasma and serum removed and stored at −80 Celsius.

After the initial evaluation tests and OST, horses received 28 grams of a SPAAB+L supplement with either a LOW or HIGH dose of polyphenol in a small amount of grain. This continued daily for six weeks.

Baseline high molecular weight (HMW) adiponectin, leptin, triglycerides (TG), non-esterified fatty acids, (NEFAs) and TNF alpha were measured both pre- and post-supplement administration. Insulin was measured at all OST time points. Differences in weight, body condition score, weight, and baseline biochemical markers (HMW adiponectin, leptin, TGs, NEFAs, and TNF alpha) were compared from pre- to post-supplement, and between HIGH and LOW dose groups, with a Student's t-test. Insulin concentrations were determined at all OST time points. Baseline, peak, 60, 75, and 90 minute concentrations, time to peak concentrations, area under the curve, were analyzed. Repeated measures mixed model ANOVAs were used to compare insulin differences between: high or low dose supplementation and pre- to post-supplement administration within a horse. Comparisons of classification of the horse as either insulin dysregulated (ID) or normal were made between pre- and post-supplementation. All significance was set at $P<0.05$.

The SPAAB+L supplement was found to be very palatable to the subject equines and no adverse effects due to the supplement were noted. Horses lost significantly more weight (FIG. 1) after supplementation and which did not differ between HIGH and LOW groups. Horses did not significantly change in their body condition scores, or in the presence of regional adiposity. No horses developed laminitis during the study.

Figure 2:
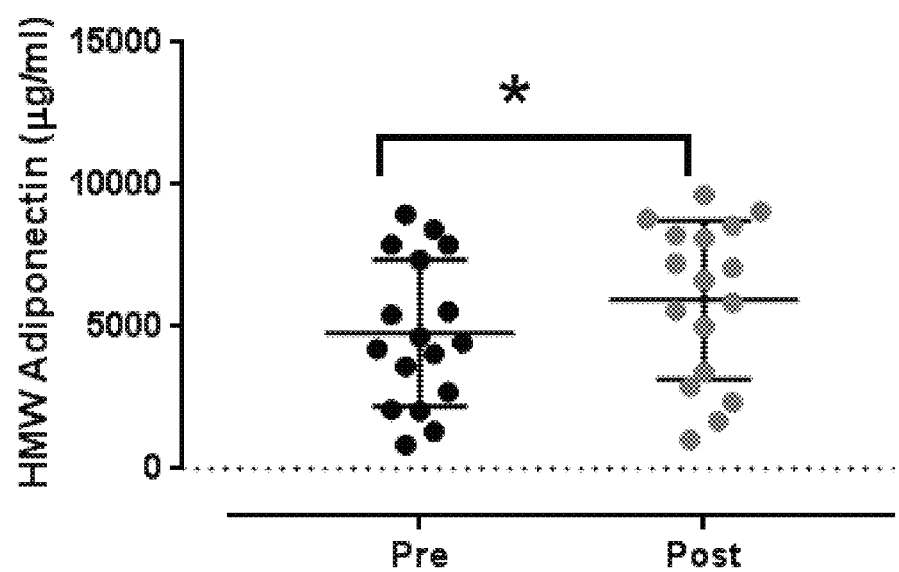
FIG. 2. HMW Adiponectin (μg/mL) both pre- and post-SPAAB+L supplementation. * indicates significant at $P<0.05$.

Horses had increased concentrations of HMW adiponectin in the post-supplementation as compared to the pre-SPB supplementation group (FIG. 2), without a significant difference between LOW and HIGH groups. There was no statistical differences in leptin, TG, NEFA, or TNF alpha concentrations between pre- and post-SPB supplementation.

Figure 3:
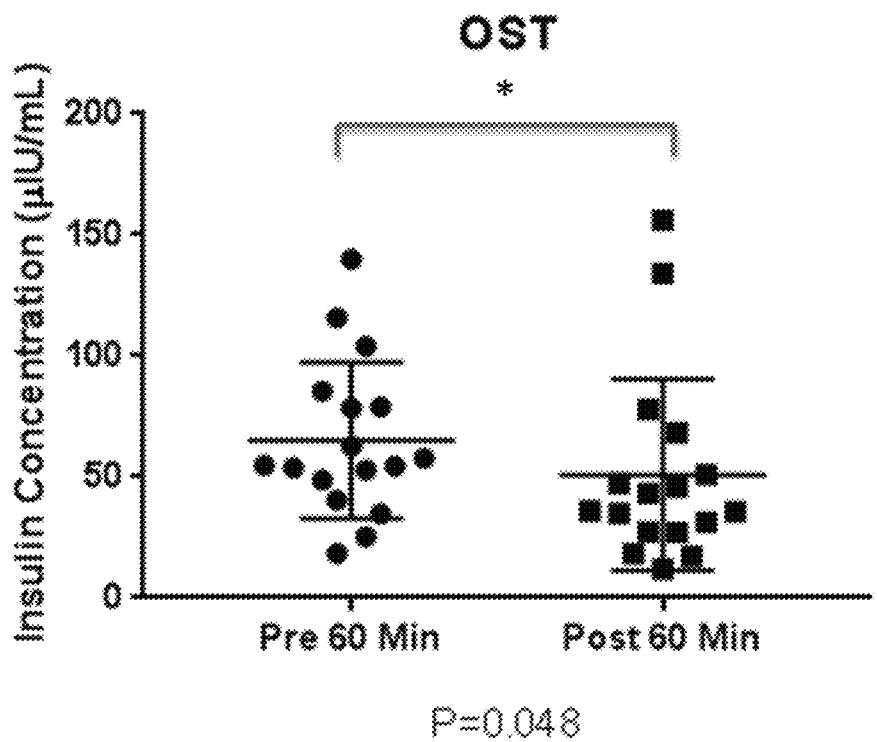
FIG. 3. Insulin Concentrations (μIU/mL) at 60 minutes post-Karo Syrup administration both pre- and post-SPAAB+L supplementation. * indicates significant at $P<0.05$.
Figure 4:
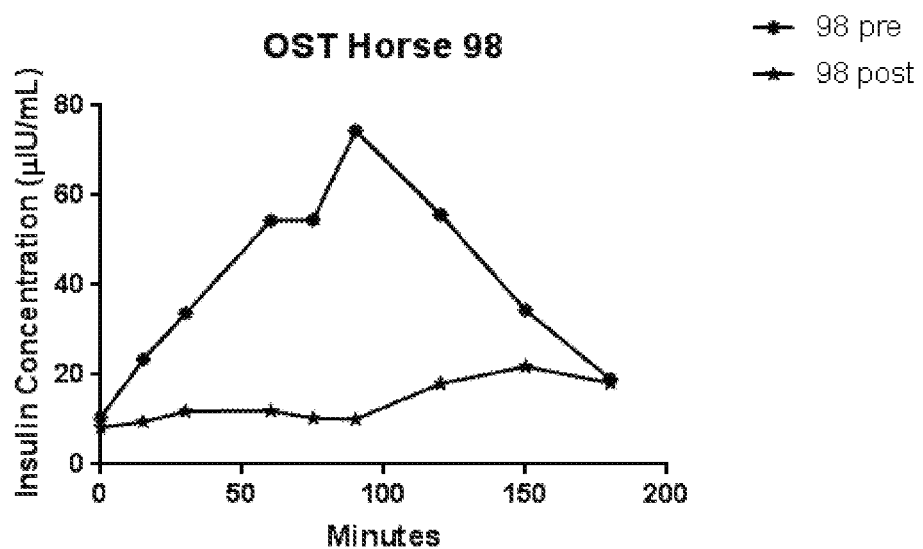
FIG. 4. Horse 98 OST Insulin concentrations (μIU/mL) pre- and post-SPAAB+L supplementation.

Horses had significantly lower insulin concentrations at 60 and 75 minutes in the post-supplementation as compared to the pre-SPB supplementation OST, but no difference between HIGH and LOW groups (FIG. 3). Indeed, horses supplemented with HIGH and LOW had significantly reduced insulin levels at 60 and 75 minutes following the OST, showing increased insulin sensitivity as a result of the administered supplements. While insulin concentrations were generally lower post-SPB supplementation, four horses actually were re-categorized from being ID to testing as normal in the OST performed post-supplementation. These horses had insulin profiles similar to that of horse 98 (FIG. 4).

As can be seen in FIG. 1, horses lost an unexpected amount of weight while on the supplement, which is believed to be due to a synergistic combination of resveratrol and the amino acid profile (particularly leucine) in the administered nutritional composition. Moreover, the weight loss appeared to be healthy weight loss, as horses had a similar body condition score at the end of the diet supplementation as when they started, suggesting that visceral adipose depots may have been reduced instead of the reduction of subcutaneous adipose depots. In horses, while multiple depots have been investigated, nuchal adipose (i.e., subcutaneous adipose) has been of most interest as the adipose reservoir active in EMS. Thus, unexpectedly, the nutritional compositions disclosed herein may reduce visceral adipose depots, which treat or reduce the risk of developing, EMS.

Horses in this example demonstrated higher concentrations of HMW adiponectin post-supplementation—suggesting an insulin sensitizing effect when coupled with the fact that there were lower insulin concentrations during the post-OST. It was surprising that significant differences were not seen with leptin, as horses in this study lost weight, and leptin is typically expected to mirror body weight changes in the horse. Also, while triglycerides have been used to predict laminitis risk, with thresholds of 57 or 94 mg/dL, in this working example, only two horses (one Arabian and one Morgan) had triglycerides higher than the lower cut off (70 mg/dL and 56 mg/dL, respectively) to begin with and this was reduced to 35.1 mg/dL in the Arabian and was at 63 mg/dL in the Morgan post-supplementation. TGs and TNF alpha were not decreased post-SPAAB+L supplementation.

While the OST has some known variability, the dramatic decrease in insulin responses seen at all time points in treated horses extends unexpectedly beyond that degree of reported variation. Clinically, insulin concentrations of >45 uIU/mL, at 60, 75, and 90 minutes are used to determine if a horse is ID, as those time points are associated with insulin peaks post-Karo syrup administration in horses. Horses after supplementation had statistically significant decreased insulin peaks at two of those three time points, with an influential point (a horse with severe ID), preventing significance at the 90 minute time point. As high insulin concentrations have been associated with laminitis development, blunting of the insulin response post an oral challenge secondary to dietary supplementation of SPAAB+L shows that the disclosed nutritional composition is unexpectedly effective to treat horses having EMS/ID and prevent or reduce risk of laminitis development.

Figure 5A:
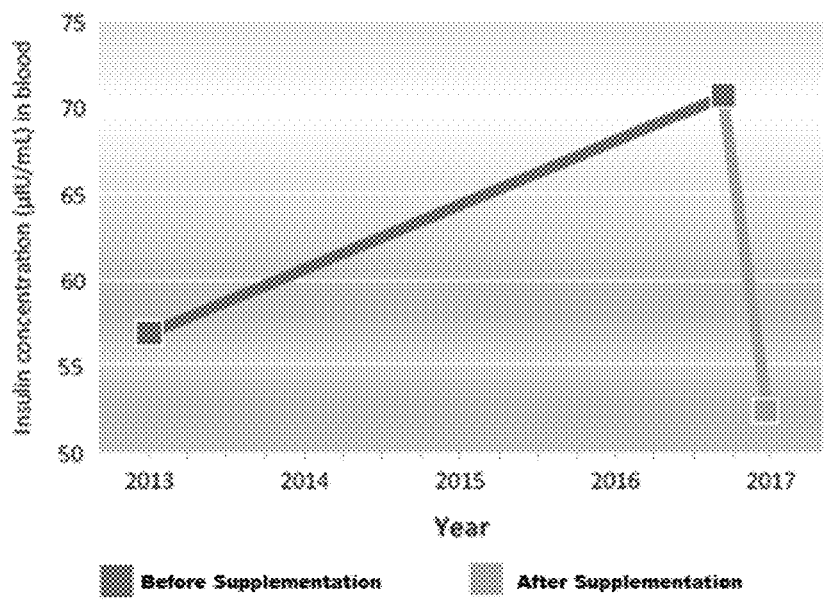
FIG. 5A. Insulin levels in horses at 60 minutes during oral sugar tests from 2013-2017.
Figure 5B:
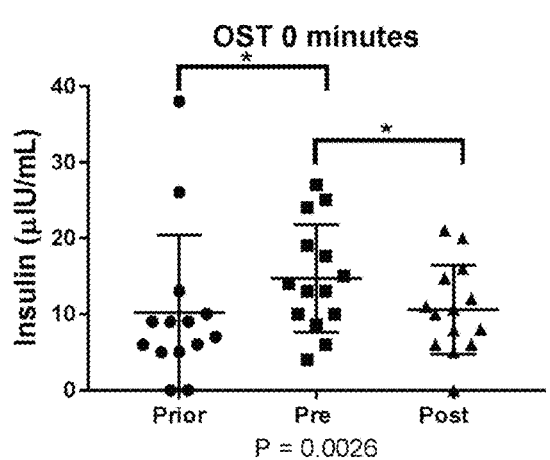
FIG. 5B. Insulin levels at OST 0 minutes in horses in 2013 compared to pre- and post-SPAAB+L supplementation in 2017. * indicates significant at $P<0.05$.
Figure 5C:
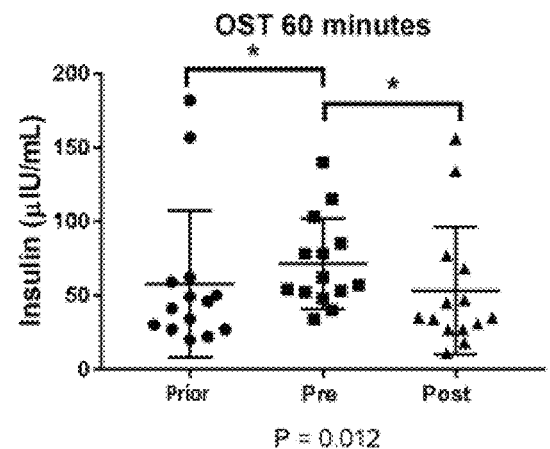
FIG. 5C. Insulin levels at OST 60 minutes in horses in 2013 compared to pre- and post-SPAAB+L supplementation in 2017. * indicates significant at $P<0.05$.

As shown in FIGS. 5A-5C, insulin dysfunction, measured by insulin concentration (μIU/mL) in blood, was tracked in horses from 2013 to 2017 without administration of the nutritional composition described herein. The 2013 level of insulin concentration is the "Prior" levels (FIGS. 5B and 5C). Insulin levels were then measured yearly as the horses aged. In the summer of 2017, the insulin concentration of the horses was measured pre-dietary supplementation of SPAAB+L ("Pre") and post pre-dietary supplementation of SPAAB+L for a 6 week period ("Post"). Post insulin concentrations were measured by OST at 0 minutes (FIG. 5B) and 60 minutes (FIG. 5C). As is shown in FIGS. 5A-5C, after the administration of the nutritional supplement, insulin levels in the horses were significantly reduced, signifying a decrease in insulin dysregulation. In fact, the insulin levels in the Post OST 60 minutes were comparable to the 2013 levels (i.e., the levels insulin observed in the horses when the horses were about four years younger), despite the fact that the horses were exhibiting progressively worse insulin dysregulation as the horses aged between 2013 and 2017.

What is claimed is:

1. A method of treating or preventing equine metabolic syndrome or equine insulin dysregulation in an equine in need thereof, comprising:
   administering to the equine a nutritional composition including a therapeutically effective amount of leucine and resveratrol.

2. The method of claim 1, wherein the nutritional composition is orally administered to the equine in an amount of from 5 g to 150 g per day.

3. The method of claim 1, wherein the nutritional composition is administered as a supplement mixed with equine feed.

4. A method of promoting health of an equine, comprising:
   administering to the equine a nutritional composition including:
      from 250 mg to 2,250 mg of resveratrol by weight of the nutritional composition;
      from 700 mg to 6,300 mg of leucine by weight of the nutritional composition; and
      from 580 mg to 5,220 mg of lysine by weight of the nutritional composition.

5. The method of claim 4, wherein the promoting health comprises one or more of: promoting glycogen repletion, aiding in exercise recovery, or treating or preventing equine metabolic syndrome, insulin dysregulation, obesity, high insulin levels, pituitary pars intermedia dysfunction, altered insulin regulation, inflammation, joint disease, high blood pressure, allergies, or a glycogen storage disease.

6. The method of claim 4, wherein the nutritional composition is administered to the equine orally on a daily dosage regimen.

7. The method of claim 1, wherein the nutritional composition further comprises:
   leucine in an amount of 0.5% to 25% of the nutritional composition by weight;
   resveratrol in an amount of 0.2% to 20% of the nutritional composition by weight; and
   one or more amino acids including alanine, glutamic acid, glycine, proline, or a combination thereof.

8. The method of claim 7, wherein the resveratrol is in an amount of from 0.5% to 10% of the nutritional composition by weight.

9. The method of claim 7, wherein the leucine is in an amount of from 1% to 15% of the nutritional composition by weight.

10. The method of claim 7, wherein the nutritional composition further comprises lysine in an amount of from 1% to 20% of the nutritional composition by weight.

11. The method of claim 7, wherein the nutritional composition further comprises quercetin.

12. The method of claim 7, wherein the nutritional composition is free or substantially free of leucine metabolites.

13. The method of claim 7, wherein the resveratrol is unencapsulated or substantially free of a carrier.

14. The method of claim 7, wherein the nutritional composition further comprises:
   4%-8% lysine of the nutritional composition by weight; and
   1%-2% quercetin of the nutritional composition by weight,
   wherein the resveratrol is in an amount of 1-3% of the nutritional composition by weight, and wherein the leucine is in an amount of from 3%-10% of the nutritional composition.

15. The method of claim 4, wherein the resveratrol is from 500 mg to 1,000 mg by weight of the nutritional composition.

16. The method of claim 4, wherein the leucine is from 1,500 mg to 2,700 mg by weight of the nutritional composition.

17. The method of claim 4, wherein the nutritional composition further comprises quercetin.

18. The method of claim 4, wherein the nutritional composition is free or substantially free of leucine metabolites.

19. The method of claim 4, wherein the resveratrol is unencapsulated or substantially free of a carrier.

20. The method of claim 4, wherein the nutritional composition comprises one or more amino acids including alanine, glutamic acid, glycine, proline, or a combination thereof.

* * * * *